US012637591B2

(12) United States Patent
Holzer et al.

(10) Patent No.: US 12,637,591 B2
(45) Date of Patent: May 26, 2026

(54) FLEXIBLE HEAT-STERILIZABLE NON-PVC MULTILAYER FILM FOR MEDICAL PACKAGINGS

(71) Applicant: PolyCine GmbH, Schiffweiler (DE)

(72) Inventors: Susanne Holzer, Ottweiler (DE); Rene Gross, Neunkirchen (DE)

(73) Assignee: POLYCINE GMBH, Schiffweiler (DE)

( * ) Notice: Subject to any disclaimer, the term of this patent is extended or adjusted under 35 U.S.C. 154(b) by 380 days.

(21) Appl. No.: 18/549,283

(22) PCT Filed: Mar. 7, 2022

(86) PCT No.: PCT/EP2022/055706
§ 371 (c)(1),
(2) Date: Sep. 6, 2023

(87) PCT Pub. No.: WO2022/189335
PCT Pub. Date: Sep. 15, 2022

(65) Prior Publication Data
US 2024/0166921 A1      May 23, 2024

(30) Foreign Application Priority Data

Mar. 9, 2021      (EP) ..................................... 21161586

(51) Int. Cl.
| | |
|---|---|
| *C09J 7/29* | (2018.01) |
| *A61L 2/04* | (2006.01) |
| *A61L 103/00* | (2026.01) |
| *A61L 103/15* | (2026.01) |
| *B32B 1/08* | (2006.01) |
| *B32B 27/08* | (2006.01) |
| *B32B 27/18* | (2006.01) |
| *B32B 27/30* | (2006.01) |
| *B32B 27/32* | (2006.01) |
| *B32B 27/36* | (2006.01) |
| *B32B 37/08* | (2006.01) |
| *B32B 37/12* | (2006.01) |
| *B65D 65/40* | (2006.01) |
| *C09J 7/38* | (2018.01) |
| *C09J 11/04* | (2006.01) |

(52) U.S. Cl.
CPC . *C09J 7/29* (2018.01); *A61L 2/04* (2013.01); *B32B 1/08* (2013.01); *B32B 27/08* (2013.01); *B32B 27/18* (2013.01); *B32B 27/302* (2013.01); *B32B 27/32* (2013.01); *B32B 27/36* (2013.01); *B32B 37/08* (2013.01); *B32B 37/12* (2013.01); *B65D 65/40* (2013.01); *C09J 7/38* (2018.01); *C09J 11/04* (2013.01); *A61L 2103/15* (2026.01); *A61L 2103/23* (2026.01); *A61L 2202/181* (2013.01); *B32B 2250/24* (2013.01); *B32B 2264/1021* (2020.08); *B32B 2270/00* (2013.01); *B32B 2274/00* (2013.01); *B32B 2307/308* (2013.01); *B32B 2307/31* (2013.01); *B32B 2307/558* (2013.01); *B32B* *2307/72* (2013.01); *B32B 2307/7376* (2023.05); *B32B 2439/46* (2013.01); *B32B 2439/80* (2013.01); *C09J 2301/162* (2020.08); *C09J 2301/302* (2020.08); *C09J 2301/414* (2020.08); *C09J 2423/046* (2013.01); *C09J 2423/106* (2013.01); *C09J 2423/166* (2013.01); *C09J 2453/006* (2013.01); *C09J 2467/00* (2013.01)

(58) Field of Classification Search
None
See application file for complete search history.

(56) References Cited

U.S. PATENT DOCUMENTS

| | | | |
|---|---|---|---|
| 2012/0034404 A1 | 2/2012 | Choi et al. | |
| 2017/0197769 A1* | 7/2017 | Unai ..................... | B32B 27/308 |
| 2022/0032592 A1 | 2/2022 | Holzer et al. | |

FOREIGN PATENT DOCUMENTS

| | | |
|---|---|---|
| DE | 20320212 U1 | 9/2004 |
| DE | 10361851 A1 | 7/2005 |
| EP | 0229475 A1 | 7/1987 |
| EP | 2231775 B1 | 9/2010 |
| JP | 2000014747 A | 1/2000 |
| JP | 2007-245490 A | 9/2007 |
| JP | 2009154332 A | 7/2009 |
| JP | 2012085742 A | 5/2012 |
| JP | 2017512672 A | 5/2017 |

(Continued)

OTHER PUBLICATIONS

Machine translation of DE 10361851 A1 (Year: 2005).*

(Continued)

*Primary Examiner* — Ramsey Zacharia

(74) *Attorney, Agent, or Firm* — Raphael Bellum PLLC

(57) ABSTRACT

Flexible, heat-sterilizable multilayer film for medical packagings, comprising (a) a first polymer layer (A) containing impact-modified propylene homopolymer; (b) a second polymer layer (B) containing: B1) 60% to 85% by weight of a homogeneous composition (B1) having a melting point of >125° C. and a density of from 945 to 960 kg/m3, composed of: B11) 65% to 85% by weight of ethylene homopolymer, and B12) 15% to 35% by weight of ethylene/C4-C12 alpha-olefin copolymer; B2) 11% to 30% by weight of propylene terpolymer; B3) 4% to 15% by weight of polyethylene elastomer (ethylene/C4-C12 alpha-olefin copolymer); c) a middle polymer layer (C) containing: C1) 61% to 80% by weight of propylene terpolymer; C2) 15% to 25% by weight of styrene block copolymer elastomer; C3) 5% to 19% by weight of polyethylene elastomer.

23 Claims, 1 Drawing Sheet

(56) References Cited

FOREIGN PATENT DOCUMENTS

| | | | |
|---|---|---|---|
| JP | 2019111805 | A | 7/2019 |
| KR | 20100101332 | A | 9/2010 |
| WO | 2009/082132 | A2 | 7/2009 |
| WO | 2020/127227 | A1 | 6/2020 |

OTHER PUBLICATIONS

International Preliminary Report on Patentability of International PCT Application No. PCT/EP2022/055706, dated Sep. 21, 2023.
International Search Report of International Application No. PCT/EP2022/055706, dated Jun. 10, 2022.

* cited by examiner

FLEXIBLE HEAT-STERILIZABLE NON-PVC MULTILAYER FILM FOR MEDICAL PACKAGINGS

TECHNICAL FIELD

The invention relates to heat-sterilizable multilayer films containing aliphatic polyolefins, to a method for producing said films and to the use of said films for production of medical packages, and also to medical packages containing such multilayer films. The multilayer films are sterilizable with hot steam and, when used for medical packages, are distinguished by a low tendency to adsorb medicaments or medical solutions, by a temperature-resistant outer layer and by sufficient adhesion between the individual layers.

BACKGROUND

Multilayer films have had a broad range of applications for many years, for example in the food industry, but also in the medical/pharmaceutical sector, for example as secondary packaging material (overpackaging) or primary packaging material for solution bags, dry concentrates and medicaments in tablet form.

Some multilayer films are processable into flexible packages which are, for example, suitable as bags for packaging and administering medical solutions. Medical solutions, for example infusion solutions for parenteral administration, in flexible disposable bags made of polyvinyl chloride (PVC) or non-PVC materials are currently on the market as standard practice.

Elastic PVC materials are hazardous to health because they contain plasticizers that can be re-released. Accordingly, there are efforts to replace PVC with non-PVC materials.

Not only must flexible medical bags have the ability to collapse, which ensures complete drainage of the bag, but they must also exhibit further performance criteria such as transparency, ability to undergo heat sterilization at 121° C., sufficient mechanical strength especially under dynamic load in the region of weld seams, good barrier to water vapor, load capacity for standard pressure-cuff applications, for example pressure infusions, and a minimal effect by the package on the bag contents from a pharmaceutical perspective.

Multilayer films having a layer structure based on polyolefins have been found to be advantageous in relation to these requirements.

DE-A 10361851 and WO 2020/127227 A1 describe a heat-sterilizable 3-ply multilayer film for producing medical bags, the outer layer of which consists of polypropylene homopolymer modified with impact modifiers, the central layer of which consists of polypropylene terpolymer modified with impact modifiers, and the inner layer of which consists of polypropylene terpolymer and/or polypropylene copolymer modified with impact modifiers. Suitable impact modifiers are styrene block copolymers (e.g. SEB) and ethylene/α-olefin copolymers. Example films have a central layer composed of 75% by weight of PP terpolymer, 20% by weight of SEBS block copolymer and 5% by weight of PE plastomer (ethylene/octene copolymer), and an inner layer composed of 85% or 75% by weight of PP terpolymer, 15% or 20% by weight of SEB block copolymer and 0% or 5% by weight of PE plastomer.

DE 203 20 212 A1 describes a heat-sterilizable 3-ply multilayer film produced by coextrusion for use for medical bags. Example films have an outer layer composed of 97% by weight of polypropylene homopolymer and 3% by weight of SEBS block copolymer, a central layer composed of 80% by weight of EXCELLEN, a heterophasic copolymer based on polypropylene and polyethylene, and 20% by weight of SEBS block copolymer, and an inner layer composed of 75% by weight of PP terpolymer, 20% by weight of SEBS block copolymer and 5% by weight of PE plastomer.

KR-A 2010-0101332 discloses multilayer films with excellent adhesion between the layers, produced by coextrusion of a polypropylene layer and a polyethylene layer, wherein the polypropylene layer is a blend with polyethylene (proportion of 40% to 50% by weight) or the polyethylene layer is a blend with polypropylene (proportion of 20% to 50% by weight).

EP-A 2231775 deals with a multilayer film for use as a container for medical solutions, preferably comprising an outer layer composed of propylene homopolymer; a central layer composed of 30% to 70% by weight of propylene-based polymer (e.g. propylene-ethylene-butene terpolymer) and 30% to 70% by weight of thermoplastic elastomer (e.g. SEBS); and an inner layer composed of 50% to 70% by weight of propylene copolymer, 5% to 20% by weight of polyethylene (e.g. HDPE) and 10% to 45% by weight of thermoplastic elastomer (e.g. SEBS).

EP-A 0229475 describes a multilayer film, preferably a 3-ply multilayer film, for medical containers, containing (a) a first (=inner) heat-sealable layer composed of a blend of preferably 40% to 70% by weight of propylene copolymer, 10% to 40% by weight of ethylene-propylene copolymer or ethylene-1-butene copolymer (proportion of 1-butene of preferably 5% to 15% by weight) and 5% to 35% by weight of elastomer (e.g. ethylene copolymer, styrene block copolymer); (b) a second (central) layer composed of a blend of (i) polyethylene (HDPE) (50% to 90% by weight) and (ii) a modifier; and (c) a third (outer) layer composed of a blend of (i) polypropylene and (ii) a modifier.

JP-A 2007/245490 describes a heat-sterilizable multilayer film for use for medical bags, containing an inner layer of high density (0.89 to 0.93 $g/cm^3$) composed of a blend of an ethylene/α-olefin copolymer-prepared by means of a metallocene catalyst—and HDPE (proportion of 10% to 40% by weight) and an outer layer composed of a propylene polymer.

US 2012/0034404 A1 describes a multilayer film for medical packages (e.g. bags) comprising: an outer layer comprising preferably a propylene homopolymer; a central layer comprising 10% to 60% by weight of a propylene copolymer and 40% to 90% by weight of a thermoplastic elastomer; and an inner layer composed of: 60% to 80% by weight of a propylene copolymer, 10% to 30% by weight of polyethylene and 1% to 10% by weight of a thermoplastic elastomer. The polyethylene is preferably a copolymer of ethylene and an α-olefin having a melting temperature of 50° C. to 120° C. (examples: 60° C.); preferably, the propylene copolymer is a propylene-ethylene-butene terpolymer. The thermoplastic elastomer used is preferably a hydrogenated styrene block copolymer.

The prior-art multilayer films still have room for improvement, especially in relation to the adhesion between the individual layers and the requirements for hot-steam sterilizability at 121° C.

It is therefore an object of the present invention to provide a flexible and heat-sterilizable multilayer film for medical purposes that has good adhesion between the individual layers and good impact strength, and additionally exhibits a low tendency to adsorb medicaments or medical solutions on the surface facing the medicament or the medical solution (inner layer), and can be processed into medical containers (e.g. bags) by simple methods.

DETAILED DESCRIPTION

Figure 1:
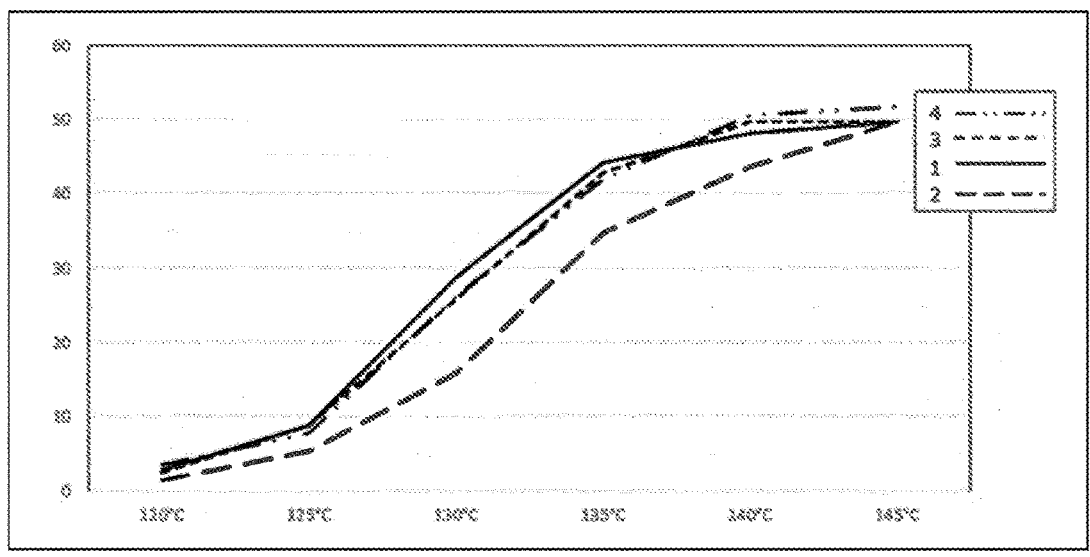
FIG. 1 shows weld curves of unsterilized samples according to the invention and comparative unsterilized samples.

The invention provides a heat-sterilizable multilayer film comprising (consisting of)
  a) a first polymer layer (A) containing (consisting of) at least one, preferably one, propylene homopolymer modified with at least one, preferably one, impact modifier;
  b) a second polymer layer (B) containing (consisting of):
    B1) 60% to 85% by weight—based on (B)—of a homogeneous composition (="composite") (B1) consisting of:
      B11) 65% to 85% by weight—based on (B1)—of ethylene homopolymer, and
      B12) 15% to 35% by weight, preferably 20% to 30% by weight-based on (B1)—of at least one ethylene copolymer which contains as comonomer at least one, preferably one, alpha-olefin having 4 to 12, preferably 4 to 8, particularly preferably 4 to 6 carbon atoms, preferably selected from 1-butene, 1-pentene, 1-hexene and 4-methyl-1-pentene, preferably 1-butene,
      and wherein composition (B1) has a melting temperature of >125° C. and a density of 945 to 960 kg/m$^3$;
    B2) 11% to 30% by weight—based on (B)—of at least one propylene terpolymer;
    B3) 4% to 15% by weight—based on (B)—of at least one polyethylene elastomer which is a copolymer of ethylene with at least one, preferably one, alpha-olefin having 4 to 12, preferably 7 to 12, carbon atoms;
  c) a central polymer layer (C) situated between the first polymer layer (A) and the second polymer layer (B), containing (consisting of):
    C1) 61% to 80% by weight, preferably 65% to 80% by weight—based on (C)—of at least one propylene terpolymer;
    C2) 15% to 25% by weight—based on (C)—of at least one styrene block copolymer elastomer;
    C3) 4% to 14% by weight, preferably 4% to 10% by weight—based on (C)—of at least one polyethylene elastomer which is a copolymer of ethylene with at least one, preferably one, alpha-olefin containing 4 to 12 carbon atoms.
The proportions indicated in percent by weight add up to 100% by weight in each case.
In the context of the present invention, the structural units of a monomer in a (co)polymer are to be understood to mean the structural units derived from the monomer incorporated by polymerization.
The term "heat-sterilizable" means that corresponding materials can be subjected to sterilization at elevated temperatures, preferably steam sterilization. Sterilization refers to methods by means of which materials and articles are cleared of living microorganisms. The state of the materials and articles that is thereby achieved is referred to as "sterile". In the case of the steam sterilization of the filled or unfilled medical packages, hot steam is used for the sterilization, which is typically carried out in an autoclave. This involves heating the medical packages for preferably 20 minutes to 121° C. at 2 bar pressure in steam. The air inside the autoclave is completely replaced by steam.

The term "multilayer film" refers to thermoplastic materials in multiple coextruded polymer layers which are joined together to form a film in the form of a running web or sleeve.

The term "impact modifier" refers to polymeric materials, such as styrene block copolymer elastomers, polyethylene elastomers and polypropylene elastomers, which as a result of blending in the melt state improve the impact strength of the polymer surrounding the impact modifier.

The term "impact strength" refers to the property of a material to withstand a dynamic load. The Izod impact strength of plastics can be measured under defined conditions in accordance with the standard DIN EN ISO 180: 2013-08.

A "homogeneous composition" is to be understood to mean a composite of substances (components) which have been mixed together at the molecular level and jointly form a single phase.

"Melting temperature" (softening temperature, $T_m$) is usually determined by means of DSC (differential scanning calorimetry).

"Density" can be determined in accordance with DIN EN ISO 1183-1 (2019-09)—Method B using a liquid pycnometer.

First Polymer Layer (A)

The first polymer layer (A) of the multilayer film according to the invention is, by definition, the polymer layer which, when processing the film into a package that is preferably a bag, is situated on the outside of the package. Therefore, it is in direct contact with the surface of the welding tool when further processing the film into packages and therefore preferably requires a high melting/softening temperature which is preferably above 125° C., particularly preferably between 127° C. and 150° C. and very particularly preferably between 130° C. and 145° C.

The first polymer layer (A) contains at least one, preferably one, polypropylene homopolymer which is modified with at least one, preferably one, impact modifier.

Preferably, the first polymer layer (A) consists of at least one, preferably one, polypropylene homopolymer which is modified with at least one, preferably one, impact modifier.

More preferably, the first polymer layer (A) contains one polypropylene homopolymer which is modified with one impact modifier.

The first polymer layer (A) contains (or consists of) at least one, preferably one, propylene homopolymer (polypropylene) which is generally modified with 1% to 30% by weight, preferably with 2% to 20% by weight, particularly preferably 2% to 10% by weight, in particular 3% to 5% by weight, of at least one impact modifier to improve (low-temperature) impact strength.

The preparation of propylene homopolymers is known. Furthermore, propylene homopolymers are commercially available, for example from Lyondell Basell Corporation, USA.

Preferably, the first polymer layer (A) contains (or consists of) a propylene homopolymer which is modified with at least one impact modifier selected from the group of styrene block copolymers such as styrene-ethylene-butylene-styrene block copolymer (SEBS), styrene-ethylenepropylene-styrene block copolymer (SEPS), styrene-ethylene-ethylene-propylene-styrene block copolymer (SEEPS), styrene-isoprene-styrene block copolymer (SIS) and styrene-butadiene-styrene block copolymer (SBS), preferably SEBS and SEPS, in particular SEBS, and/or from the group of copolymers of ethylene with at least one alpha-olefin having 4 to 12, preferably 4 to 8, carbon atoms such as ethylene-butylene copolymers and/or ethylene-1-octene copolymers.

Particularly preferably, the first polymer layer (A) contains (or consists of) 90% to 98% by weight, in particular 95% to 97% by weight, of a propylene homopolymer and 2% to 10% by weight, in particular 3% to 5% by weight, of a styrene block copolymer and/or a copolymer of ethylene with at least one alpha-olefin having 4 to 12, preferably 4 to 8, carbon atoms.

In a preferred embodiment, the first polymer layer (A) contains (or consists of) 95% to 97% by weight of a polypropylene homopolymer and 3% to 5% by weight of a styrene-ethylene/butylene block copolymer.

The specified weights for the components of the first polymer layer (A) are based on the total weight of the first polymer layer (A).

Second Polymer Layer (B)

The second polymer layer (B) is, by definition, the polymer layer which, when processing the multilayer film according to the invention into a package that is preferably a bag, is situated on the inside of the package. Said polymer layer is responsible for the ability to tightly seal the package by heat sealing. The second polymer layer (B) of the film must be heat-sealable with itself and with appropriately inserted port elements in a secure manner and at a lowest possible temperature and with a shortest possible welding time and nevertheless be heat-sterilizable at temperatures of greater than 121° C. A low welding temperature is particularly important for minimizing structural stresses on the film structure. Therefore, the melting/softening temperature of the second polymer layer (B) is generally above 121° C., preferably between 122° C. and 135° C., particularly preferably between 124° C. and 130° C., but in any case below the melting/softening temperature of the first polymer layer (A).

The second polymer layer (B) of the multilayer film according to the invention contains (or consists of) components B1), B2) and B3) in the following proportions (based in each case on (B)):

B1) 60% to 85% by weight, preferably 65% to 80% by weight, particularly preferably 72% to 78% by weight, B2) 11% to 30% by weight, preferably 15% to 25% by weight, particularly preferably 17% to 22% by weight;

B3) 4% to 15% by weight, preferably 4% to 12% by weight, particularly preferably 5% to 10% by weight.

Component B1)

Component B1) is used to reduce the tendency of delamination between the second polymer layer (B) and the central polymer layer (C).

The homogeneous composition (="composite") (B1) consists of:

B11) 65% to 85% by weight—based on (B1)—of ethylene homopolymer, and

B12) 15% to 35% by weight, preferably 20% to 30% by weight—based on (B1)—of at least one, preferably one, ethylene copolymer which contains as comonomer at least one, preferably one, alpha-olefin having 4 to 12, preferably 4 to 8, particularly preferably 4 to 6 carbon atoms, very particularly preferably selected from 1-butene, 1-pentene, 1-hexene and 4-methyl-1-pentene, preferably 1-butene.

The homogeneous composition (B1) has a melting temperature of >125° C., preferably of 130° C. to 135° C., and a density of 945 to 960 kg/m³.

The ethylene copolymer B12) does not contain further comonomers in addition to the alpha-olefin having 4 to 12 carbon atoms.

The proportion of the alpha-olefin comonomer-based on (B12)—is generally 25% to 40% by weight, preferably 30% to 37% by weight; the ethylene proportion-based on (B12)—is accordingly 60% to 75% by weight, preferably 63% to 70% by weight. The proportions by weight are based in each case on the structural units of the monomers incorporated into the ethylene copolymer (B12) by polymerization.

Preferably, component B1) is a homogeneous composition consisting of:

B11) 70% to 80% by weight—based on (B1)—of ethylene homopolymer, and

B12) 20% to 30% by weight—based on (B1)—of least one, preferably one, ethylene copolymer which contains as comonomer at least one, preferably one, alpha-olefin selected from 1-butene, 1-pentene, 1-hexene and 4-methyl-1-pentene, preferably 1-butene.

Particularly preferably, component B1) is a homogeneous composition consisting of:

B11) 70% to 80% by weight—based on (B1)—of ethylene homopolymer, and

B12) 20% to 30% by weight—based on (B1)—of ethylene-1-butene copolymer, in which the proportion of 1-butene-based on (B12)—is 25% to 40% by weight, preferably 30% to 37% by weight.

The ethylene homopolymer B11) used is generally a high-density polyethylene (HDPE), preferably an HDPE having a density of 950 to 970 kg/m³.

The preparation of HDPE is known to a person skilled in the art.

Furthermore, HDPE is commercially available; HDPE having a density of 950 to 970 kg/m³ is, for example, available as Nipolon® Hard from Tosoh Co., Ltd. or as Bormed® HE2581-PH and Bormed HE7541-PH from Borealis.

The ethylene copolymer B12) is usually prepared by copolymerization of ethylene and the alpha-olefin comonomer by means of a metallocene catalyst.

Suitable metallocene catalysts are organic compounds of a transition metal having multiple (number in line with the valency of the transition metal) ligands coordinated with the transition metal, of which at least one ligand is a cyclopentadienyl radical. The transition metal is preferably selected from the group consisting of Zr, Ti, Hf, V, Nb, Tn and Cr, and is particularly preferably Zr or Hf, very particularly preferably Zr. Preference is given to a Zr or Hf metallocene catalyst having two cyclopentadienyl radicals.

Particular preference is given to the metallocene catalyst bis(n-butylcylopentadienyl) zirconium dichloride.

The ethylene copolymer B12) is prepared by using the aforementioned metallocene catalysts as ionic complexes, which can be obtained by reaction of the metallocene catalyst with organically modified alumina. The alumina used can be all customary clay materials; preference is given to hectorite, smectite, and montmorillonite.

The organically modified alumina is obtained by reaction of alumina with an aliphatic salt. Examples of such an aliphatic salt are N,N-dimethyldecylamine hydrochloride, N, N-dimethyldodecylamine hydrochloride, N, N-dimethyltetradecylamine hydrochloride, N, N-dimethylhexadecylamine hydrochloride, N, N-dimethyloctadodecylamine hydrochloride, N,N-dimethylbehenylamine hydrochloride, N, N-dimethylbehenylamine hydrofluoride, N,N-dimethylbehenylamine hydrobromide and N,N-dimethylbehenylamine hydroiodide; preference is given to N,N-dimethylbehenylamine hydrochloride.

Preferably, the ethylene copolymer B12) is prepared by additionally using an organoaluminum compound, preferably triisobutylaluminum, as co-catalyst.

The ethylene copolymer B12) can be prepared in the presence of the metallocene catalyst, for example by a slurry process, a solution process or in the gas phase.

The preparation of ethylene-alpha-olefin copolymers by means of such a metallocene catalyst is, for example, described in JP-A 2019/111805 and JP-A 2019/167430.

The ethylene copolymer B12) is a high-density ethylene copolymer. Preferably, the ethylene copolymer B12) has a density of 945 to 960 kg/m³.

Component B2)

Component B2) is at least one, preferably one, propylene terpolymer.

The term "terpolymer" denotes a copolymer which has been prepared from three different monomers.

The term "propylene terpolymer" refers to a polypropylene molecular chain modified with two additional comonomers in the polymerization process. Preferred additional comonomers are ethylene and/or at least one C4-C12 α-olefin, preferably C4-C8 α-olefin, particularly preferably ethylene and a C4-C8 α-olefin, very particularly preferably ethylene and 1-butene.

Based in each case on (B2), the proportion of ethylene is preferably 1% to 4% by weight and the proportion of the at least one C4-C8 α-olefin, in particular 1-butene, is preferably 9% to 12% by weight. The proportions by weight are based in each case on the structural units of the monomers incorporated into the terpolymer (B2) by polymerization.

Very particularly preferably propylene terpolymer (B2) made up of structural units of propylene, ethylene and butylene.

The preparation of propylene terpolymers is known. Furthermore, suitable propylene terpolymers are commercially available, for example from Borealis, Austria.

Component B3)

Component B3) is at least one, preferably one, polyethylene elastomer which is a copolymer of ethylene with at least one, preferably one, alpha-olefin having 4 to 12, preferably 7 to 12, very particularly preferably 8 carbon atoms.

Ethylene/alpha-olefin copolymers B3) preferably have a density in the range from 600 to 950 kg/m³, particularly preferably 750 to 900 kg/m³.

The proportion of the structural units of the alpha-olefin incorporated by polymerization—based on (B3)—is more than 8% by weight, preferably more than 10% by weight, in particular 20% to 30% by weight.

Preferably, component B3) is an ethylene-1-octene copolymer.

Suitable polyethylene elastomers are commercially available, for example from Dow Chemical Company, USA.

Preferably, the second polymer layer (B) according to the invention contains (or consists of) a homogeneous composition (component B1) consisting of B11) 70% to 80% by weight of high-density polyethylene and B12) 20% to 30% by weight of ethylene-1-butene copolymer, a propylene terpolymer (component B2) made up of structural units of propylene, ethylene and butylene (component B2), and an ethylene-1-octene copolymer (component B3).

Particularly preferably, the second polymer layer (B) according to the invention contains (or consists of) 65% to 80% by weight, preferably 72% to 78% by weight of the homogeneous composition (component B1) consisting of B11) 70% to 80% by weight of high-density polyethylene and B12) 20% to 30% by weight of ethylene-1-butene copolymer, 15% to 25% by weight, preferably 17% to 22% by weight of propylene terpolymer (component B2) made up of structural units of propylene, ethylene and butylene (component B2), and 4% to 12% by weight, preferably 5% to 10% by weight of ethylene-1-octene copolymer (component B3).

The specified weights for components B1), B2) and B3) of the second polymer layer (B) are based on the total weight of the second polymer layer (B).

Central Polymer Layer (C)

The central polymer layer (C) has the largest proportion by mass (at least 50% by weight) of the multilayer film, preferably 60% to 95% by weight, particularly preferably 70% to 90% by weight, very particularly preferably 75% to 85% by weight of the entire multilayer film, and is used to improve the impact strength of the overall structure.

The central polymer layer (C) of the multilayer film according to the invention contains (or consists of) components C1), C2) and C3) in the following proportions (based in each case on (C)):

C1) 61% to 80% by weight, preferably 65% to 75% by weight,

C2) 15% to 25% by weight, preferably 17% to 22% by weight,

C3) 5% to 19% by weight, preferably 8% to 17% by weight.

Component C1)

Component C1) is at least one, preferably one, propylene terpolymer. Propylene terpolymer C1) has been defined as component B2); reference is made to the relevant discussions in relation to component B2).

Component C2)

Component C2) is at least one, preferably one, styrene block copolymer (SBC) elastomer.

The term "styrene block copolymer elastomer" refers to synthetic thermoplastic elastomers based on styrene block copolymers that are used as impact modifiers. The at least one styrene block copolymer (SBC) elastomer B2) is preferably selected from the group consisting of: styrene-ethylene-butylene-styrene block copolymer (SEBS), styrene-ethylene-propylene-styrene block copolymer (SEPS), styrene-ethylene-ethylene-propylene-styrene block copolymer (SEEPS), styrene-isoprene-styrene block copolymer (SIS) and styrene-butadiene-styrene block copolymer (SBS), preferably SEBS and SEPS, in particular SEBS.

Suitable styrene block copolymer (SBC) elastomers C2) are commercially available, for example from Asahi Kasei, Japan.

It is also possible to partially replace the styrene block copolymer (SBC) elastomer with one or more thermoplastic olefin-based elastomers (TPE-O) (proportion of TPE-O: not more than 45% by weight, preferably 20% to 30% by weight).

Preferably, component C2) is a styrene block copolymer (SBC) elastomer which does not contain any proportions of a thermoplastic olefin-based elastomer.

9
10

Component C3)

Component C3) is at least one, preferably one, polyethylene elastomer which is a copolymer of ethylene with at least one alpha-olefin having 4 to 12, preferably 4 to 8 carbon atoms.

Ethylene/alpha-olefin copolymers (C3) generally have a density in the range from 440 to 860 kg/m³.

The proportion of the structural units of the alpha-olefin incorporated by polymerization—based on (C3)—is more than 8% by weight, preferably more than 10% by weight, in particular 20% to 30% by weight.

Preferably, component C3) is an ethylene-1-butene copolymer, an ethylene-1-hexene copolymer or an ethylene-1-octene copolymer, particularly preferably an ethylene-1-octene copolymer.

Suitable polyethylene elastomers are commercially available, for example from Dow Chemical Company, USA.

Preferably, the central polymer layer (C) according to the invention contains (or consists of) a propylene terpolymer (component C1)) made up of structural units of propylene, ethylene and butylene, a styrene-ethylene-butylene-styrene block copolymer (SEBS) (component C2)), and an ethylene-octene copolymer (component C3)).

Particularly preferably, the central polymer layer (C) according to the invention contains (or consists of) 65% to 80% by weight, preferably 72% to 78% by weight of propylene terpolymer (component C1)) made up of structural units of propylene, ethylene and butylene, 17% to 22% by weight, preferably 19% to 21% by weight of styrene-ethylene-butylene-styrene block copolymer (SEBS) (component C2)); and 4% to 10% by weight, preferably 5% to 8% by weight of ethylene-octene copolymer (component C3)).

Functional Layer (D)

The heat-sterilizable multilayer film according to the invention can further comprise an additional functional layer D) as an outer layer which is adjacent to the first polymer layer (A) on the outer side of (A) (i.e. on the other side of (A) opposite the side with polymer layer (C)).

Functional layer (D) preferably makes the heat-sterilizable multilayer film, and packages such as medical bags produced therefrom or film sleeves produced therefrom, gasproof and/or waterproof.

Functional layer D) contains, preferably consists of, at least one, preferably one, material selected from the group consisting of: ethylene-vinyl alcohol copolymers, polyvinyl alcohols, polyamides, liquid crystal polymers (LCP), aromatic polyesters, preferably terephthalic acid polyesters, particularly preferably polyethylene terephthalates (PET), silicon oxide ($SiO_x$), aluminum oxide ($AlO_x$) and acrylate-based polymers.

Preferably, the functional layer (D) consists of PET/$SiO_x$.

The functional layer (D) preferably has a layer thickness of 5 to 25 μm, in particular of 10 to 20 μm.

A functional layer (D) composed of PET/$SiO_x$ significantly improves the gas barrier (e.g. the oxygen barrier) of the heat-sterilizable multilayer film according to the invention, and so the film is also highly suitable for the storage of oxygen-sensitive ingredients.

A $SiO_x$/PET functional layer (D) can lower the oxygen barrier or oxygen transmission rate (OTR) of the heat-sterilizable multilayer film according to the invention by a factor of 1000 to OTR values<1 cm³/(m²×day) ASTM F1927 (23° C., 50% RH).

Multilayer Film

Preferably, the heat-sterilizable multilayer film according to the invention consists of the polymer layers (A), (B) and (C).

In each of the polymer layers (A), (B) and (C), the multilayer film can contain customary amounts of customary additives and/or processing aids that are suitable for the intended use of the multilayer film.

Preferred additives are antioxidants and thermal stabilizers (phosphitic and phenolic stabilizers such as Irgafos® 168, Irgafos P-EPQ, Irganox® 1076 or Irganox 1010), and also acid scavengers such as DHT-4A®, synthetic hydrotalcite (SHT) and magnesium oxide (MgO).

Preferably, the heat-sterilizable multilayer film composed of the polymer layers (A), (B) and (C) according to the invention contains at least one antioxidant, thermal stabilizer and/or acid scavenger, preferably in a total amount of <3000 ppm, based on the entire multilayer film.

Preferably, the polymer layers (A), (B) and (C) adhere to one another without use of an adhesion promoter, i.e. the multilayer film according to the invention composed of the polymer layers (A), (B) and (C) preferably does not contain an adhesion promoter. Furthermore, preferably at least the second polymer layer (B) does not contain further additives and/or processing aids (e.g. modifiers or plasticizers, such as mineral oil), very particular preference being given to none of the polymer layers (A), (B) and (C) containing further additives and/or processing aids in addition to the additives mentioned above. Accordingly, the medicament or the medical solution is not affected or hardly affected by the multilayer film according to the invention as packaging material during sterilization and storage.

In the case of a multilayer film according to the invention consisting of the polymer layers (A), (B), (C) and the functional layer (D), the multilayer film generally contains an adhesion promoter or pressure-sensitive adhesive in addition to the additives mentioned above as preferred.

The layer thickness of the first polymer layer (A) is generally 5% to 15% by weight, preferably 7% to 13% by weight, particularly preferably 7.5% to 10% by weight, of the total film thickness of the multilayer film according to the invention.

The layer thickness of the second polymer layer (B) is generally 5% to 15% by weight, preferably 7% to 13% by weight, particularly preferably 7.5% to 10% by weight, of the total film thickness of the multilayer film according to the invention.

The central polymer layer (C) has the largest proportion (preferably at least 70% by weight of the total film thickness) of the multilayer film according to the invention and is used to improve the impact strength of the overall structure.

If present, the layer thickness of the optional functional layer (D) is preferably 2.5% to 12.5% by weight, particularly preferably 5% to 10% by weight, of the total film thickness of the multilayer film according to the invention.

The total film thickness of the multilayer film according to the invention is preferably 50 to 500 μm, particularly preferably 100 to 400 μm, very particularly preferably 150 to 300 μm.

The total film thickness of a multilayer film according to the invention consisting of the polymer layers (A), (B) and (C) is preferably 50 to 500 μm, particularly preferably 100 to 400 μm, very particularly preferably 150 to 300 μm.

Particular preference is given to a multilayer film according to the invention which consists of the polymer layers (A), (B) and (C) and is characterized in that the total film thickness of the multilayer film is 50 to 500 μm, particularly preferably 100 to 400 μm, and—based in each case on the total film thickness of the multilayer film— the layer thickness of the first polymer layer (A) is 5% to 15% by weight, preferably 7% to 13% by weight, the layer thickness of the second polymer layer (B) is 5% to 15% by weight, preferably 7% to 13% by weight; and the layer thickness of the central polymer layer (C) is 70% to 85% by weight, preferably 74% to 80% by weight; and the proportions of (A), (B) and (C) add up to 100% by weight in each case.

Method for Producing the Multilayer Film

The invention further provides a method for producing the multilayer film according to the invention, wherein the first polymer layer (A), the central polymer layer (C) and the second polymer layer (B) are coextruded.

Coextrusion comprises bringing together the plastics melts of the polymer layers (A), (B) and (C) before they leave the profile die of an extruder to form the multilayer film according to the invention.

In many cases, the extrusion process is a two-stage process. In a first step, the materials used for the individual polymer layers are mixed and compacted in extruders, preferably parallel twin-screw extruders (compounders), heating/cooling mixers or pellet presses. The plastics melts of the polymer layers (A), (B) and (C) are then brought together in another extruder, which is directly coupled or spatially and temporally separated, before they leave the profile die to form the multilayer film according to the invention.

Preferably, the multilayer film obtained by the method according to the invention is shock-cooled with water.

The coextrusion can yield the multilayer film according to the invention in the form of a flat film (flat film method, for example when using a slot die) or a film sleeve (blown film method, for example flooding the interior of the film sleeve with—preferably sterile-filtered-air), with, in the case of a film sleeve, the outside consisting of the first polymer layer (A) and the inside consisting of the second polymer layer (B).

In a further method step, the optional functional layer (D) can be applied to the multilayer film obtained by the method according to the invention, for example by hot lamination or preferably by lamination.

According to a particular embodiment for producing a laminated multilayer film sleeve according to the invention, the method according to the invention comprises the following steps:

(a') producing a film sleeve made of the multilayer film according to the invention by coextrusion of the first polymer layer (A), the central polymer layer (C) and the second polymer layer (B), wherein the interior of the film sleeve is flooded with—preferably sterile-filtered—air;

(b') optionally cooling the film sleeve produced in method step (a');

(c') coating the optionally cooled film sleeve with a pressure-sensitive adhesive layer on at least one side (first polymer layer (A)) of the film sleeve;

(d') optionally drying the film sleeve provided with the pressure-sensitive adhesive layer;

(e') laminating the at least one side (first polymer layer (A)) of the film sleeve coated with the pressure-sensitive adhesive layer with a functional layer (D), in particular a SiO$_x$/PET functional layer;

(f) optionally drying and curing the laminated film sleeve.

According to the aforementioned embodiment of the method according to the invention, the two parallel inner sides (=second polymer layers (B)) of the film sleeve preferably directly adhere on top of one another after the melt extrusion or coextrusion of the film sleeve, and so it is possible to coat the outer faces (first polymer layers (A)) of the film sleeve while the interior of the film sleeve is closed. The closed interior, which is inflated when the resultant film sleeve is used later, is thus substantially particle-free.

Preferably, in the aforementioned embodiment of the method according to the invention, the interior of the film sleeve is flooded with sterile-filtered air, thus maintaining a laminated multilayer film sleeve which is low in particles and is particularly highly suitable for medical purposes.

Particularly preferably, a laminated multilayer film sleeve which is low in particles is produced by carrying out the aforementioned method according to the invention in a clean room.

In the above embodiment of the method according to the invention, an adhesion promoter allowing complete curing at room temperature after about 2 weeks, preferably 1 week, is preferably used. In a heat chamber, the curing can also be achieved more rapidly at elevated temperature, preferably 30° C. or higher, in many cases 40° C. to 60° C.

Suitable adhesion promoters (pressure-sensitive adhesives, adhesives or laminating adhesives) are, for example, isocyanates, polyurethanes, poly(ethyl acrylate/methacrylic ester), pure acrylate copolymers, vinyl ester/acrylate copolymers or inorganic-organic hybrid polymers.

Preferred adhesion promoters are two-component systems, which can be solvent-based or solvent-free, and silane-based or silane-free, and can be optionally used with an additional "catalyst" to accelerate curing.

Suitable solvent-based two-component systems are, for example, polyurethane adhesives, including commercially available systems such as Dow ADCOTE™ 675A+ADCOTE™ 675C coreactant;

Dow ADCOTE 811A+ADCOTE 811B coreactant;

Dow ADCOTE E735A-75+ADCOTE™ E735C2 coreactant:

MORCHEM PS 241 AE+CS-97 coreactant,

Henkel Loctite Liofol LA2798+Henkel Loctite Liofol LA7371;

Henkel LOCTITE HY 4070 2K hybrid adhesive.

The aforementioned systems can be optionally used with "catalysts", including those such as Dow Catalyst 9L10 (polyisocyanate), Dow Catalyst 9L200 and Dow Catalyst F Adcote 40-3E, which are commercially available.

Suitable solvent-free two-component systems are, for example, polyurethane adhesives, including commercially available systems such as Dow MOR-FREE™ L 75-720 adhesive+CR 88-720 or CR 88-721 or MOR-FREE™ C 79 S coreactant Dow MOR-FREE™ 203A adhesive+MOR-FREE™ 200C coreactant Dow MOR-FREE™ L705 adhesive+MOR-FREE™ C 79 or MOR-FREE™ C-102 coreactant.

Alternatively, the adhesion promoters used can also be one-component systems, which can be solvent-based or solvent-free, and silane-based or silane-free, and can be optionally used with an additional "catalyst" to accelerate curing.

Suitable solvent-free one-component systems are, for example, Dow MOR-FREE™ ELM 415A (polyurethane adhesive) or SENOBOND® WB FILM LAMINATING ADHESIVE FP NDC 375224, which are commercially available.

Particularly preferably, the adhesive is chosen such that it complies with the requirements of pharmacopeia limits, for example with respect to migration properties, and is preferably free of organic solvents.

Depending on the procedure or desired coating, the adhesive layer can be applied to one side or both sides of the film sleeve produced by coextrusion. This can be done, for example, by spraying or knife coating. Also suitable is the use of aqueous solutions of the relevant adhesive agents.

After said adhesive layers have been applied, the resultant film sleeve can be optionally dried. For example, if the adhesive is applied using water, the drying can be carried out by evaporation of the water.

The layer thicknesses of the pressure-sensitive adhesive layers are preferably in the range from 3 to 10 μm.

The invention additionally provides for the use of the multilayer film according to the invention for producing a medical package, preferably a medical bag.

Also provided for by the invention is the use of the medical package according to the invention as a container for at least one medicament.

The medical package according to the invention is especially suitable as a container for at least one medicament, where the combination of a polypropylene-based outer and central layer (polymer layers (A) and (C)) with a polyethylene-based inner layer (polymer layer (B)) means that very good processability on all common bag sealing machines is ensured and that, at the same time, the polyethylene of the inner layer has a particularly low tendency to adsorb active medical ingredients.

In a preferred embodiment, the package according to the invention is subdivided into chambers, thus allowing use thereof as a container for a plurality of medicaments at the same time. This is relevant, for example, for those combinations of medicaments that have to be administered together, but are not stable in combination over long periods of time, or for solid medicaments that are administered in the form of a solution or suspension, but not are not stable in the solution or suspension for long periods of time. The constituents of the final dosage form can be stored separately by means of separate chambers and mixed with one another shortly before administration by opening the separation points.

A method for producing a medical package according to the invention, preferably a bag, comprises the steps of:

a) providing at least one heat-sterilizable multilayer film according to the invention;

b) optionally providing one or more port elements and/or flexible tubes;

c) shaping a medical package, preferably a bag, from the at least one heat-sterilizable multilayer film, such that the second polymer layer (B) forms the inner face of the medical package, preferably the bag, and the first polymer layer (A) forms the outer face of the medical package, preferably the bag;

d) optionally positioning the port elements and/or flexible tubes between the inner faces at the contours of the medical package, preferably the bag;

e) contacting the inner faces with one other and with port elements and/or flexible tubes optionally positioned in between at the contours of the medical package, preferably the bag;

f) heat-sealing the inner faces with one another and with port elements and/or flexible tubes optionally positioned in between at the contours of the medical package, preferably the bag.

In step a), the multilayer film according to the invention is preferably provided in the form of a flat film or a tubular film. Depending on the form of the film that is provided, the remainder of the method can differ in specific details. The film sleeve low in particles that is obtained can be laminated with a functional layer (D), for example a SiOx/PET functional layer, by means of additional method steps.

Depending on the use of the medical package according to the invention, preferably the bag, additional elements, such as for example port elements and/or flexible tubes, can be optionally provided in step b) in the method after the multilayer film according to the invention has been provided. Providing these elements is useful, for example, if the medical package according to the invention, preferably the bag, is to be used as a fixed component of a medical device or is to be connected to a medical device. Omitting step b) can be useful, for example, if the medical package, preferably the bag, is used solely for storage of a medicament and is damaged to withdraw the medicament, for example by tearing open or piercing with a cannula.

In step c), the provided multilayer film according to the invention is brought into the form of a medical package, preferably a bag. If a tubular film was provided in step a), the shaping of the medical package, preferably the bag, can, for example, include only the cutting of the tubular film to the desired length, since the second polymer layer (B) already forms the inner face of the tubular film and the first polymer layer (A) the outer face of the tubular film. If a flat film was provided in step a), the medical package, preferably the bag, can, for example, be shaped from one piece of multilayer film in step c) by cutting said piece into a mirror-symmetrical shape and folding it down along the mirror axis, such that the edges of the film lie on top of one another congruently, with the second polymer layer (B) on the inside. Alternatively, the medical package according to the invention, preferably the bag, can, for example, be shaped from two pieces of flat film by cutting the two pieces mirror-symmetrically to one another and placing them congruently on top of one another, with the second polymer layer (B) on the inside. Rectangular shapes are particularly preferred for cutting, since this results in the least material loss and the simplest processability. However, other shapes are also possible, for example it is possible to produce a medical package, preferably a bag, having an aesthetic shape that is appealing to children and distracts them from the actual administration of a medicament.

Depending on whether additional elements such as port elements and/or flexible tubes were provided in step b), said elements can be positioned between the inner faces at the contours of the shaped medical package, preferably the bag, in step d). In the case of a tubular film, this means the insertion of the additional elements into the openings of the tubular film. Here, the elements can be positioned only on two opposite sides of the medical package, preferably the bag. In the case of a flat film, the insertion of the additional elements between the edges of the one or more pieces of flat film that were laid on top of one another congruently in step c) is meant. Here, the elements can be positioned at any points along the edges, most preferably at two opposing edges.

In step e), the inner faces of the shaped medical package, preferably the bag, are contacted with one another and with the additional elements optionally situated between the inner faces at the contours of said bag so that said inner faces can be sealed together by supply of heat and optionally mechanical pressure in step f). With the heat-sealing, the temperature is preferably chosen such that it lies above the melting/softening point of the second polymer layer (B), but below the melting/softening point of the first polymer layer (A). This makes it possible to ensure that the second polymer layer (B) melts at the contours of the medical package, preferably the bag, thereby closing it permanently and fluid-tightly, whereas the first polymer layer (A) retains its shape, thereby maintaining the stability of the medical package, preferably the bag.

An important criterion for the use of the multilayer film according to the invention as primary packaging material for medical solutions is the barrier effect against loss of liquid. Such loss of liquid results in concentration of the active ingredients in solution, which loss of liquid must not exceed specific values. Loss of liquid during storage determines, inter alia, the shelf life of the product. The formulation of the multilayer film according to the invention is chosen such that a very good water vapor barrier is achieved together with good impact strength.

The multilayer film according to the invention is distinguished by the fact that it is heat-sterilizable, impact-resistant and flexible (without plasticizer) and is securely heat-sealable even with port elements by means of a continuous-heat welding method, and that it additionally has good adhesion between the individual layers without requiring an adhesion promoter and medical solutions or medicaments are not affected or are at least hardly affected.

Multilayer films according to the invention provided with an additional functional layer (D), in particular a SiO$_x$/PET functional layer, have a distinctly improved gas barrier which also makes it possible to store oxygen-sensitive ingredients.

The invention will be more particularly elucidated below on the basis of examples without being limited thereby.

Example 1

First Polymer Layer (A):
  97% by weight of Moplen® HP525J from Lyondell Basell Corp., USA/propylene homopolymer
  3% by weight of Tuftec® H1062 from Asahi Kasei, Japan/styrene-ethylene/butylene block copolymer
  The stated formulation was homogeneously mixed in the melt state in a separate compounding step, extruded, and granulated for further use.
Second Polymer Layer (B):
  B1) 75% by weight of Tosoh FY-13 from Tosoh Corp., Japan//composite composed of ethylene homopolymer (70% to 80% by weight) and ethylene-1-butene copolymer (20% to 30% by weight)/density: 950 kg/m³, T$_m$: 128° C.
  B2) 20% by weight of Bormed® TD109CF from Borealis, Austria/propylene terpolymer
  B3) 5% by weight of Engage® 8003 from Dow Chemical Company, USA/ethylene-octene polyolefin elastomer
  The stated formulation was homogeneously mixed in the melt state in a separate compounding step, extruded, and granulated for further use.
Central Polymer Layer (C):
  C1) 70% by weight of Bormed® TD109CF from Borealis, Austria/propylene terpolymer
  C2) 20% by weight of Tuftec® H1062 from Asahi Kasei, Japan/styrene-ethylene/butylene block copolymer
  C3) 10% by weight of Engage® 8003 from Dow Chemical Company, USA/ethylene-octene polyolefin elastomer
  The stated formulation was homogeneously mixed in the melt state in a separate compounding step, extruded, and granulated for further use.
  The melts from the granulated compounds of the first polymer layer (A), the central polymer layer (C) and the second polymer layer (B) were coextruded on a blown-film line with water cooling using process parameters customary for polypropylene, and a multilayer film was obtained in the form of a film sleeve, the interior of which was flooded with sterile-filtered air.

The film was made with a total thickness of 200 μm, with the first polymer layer (A) and second polymer layer (B) both having a thickness of 15 μm and the central polymer layer (C) having a thickness of 170 μm.

The film produced is sterilizable with hot steam and is already permanently heat-sealable with welding tools adjusted to a temperature of 125° C.

Example 2

A film sleeve produced according to Example 1 was additionally provided with a functional layer (D) composed of SiO$_x$/PET (Techbarrier T from Mitsubishi) on both sides in a layer thickness of 15 μm in each case.

A two-component adhesive (Dow ADCOTE 811A+AD-COTE 811B coreactant, and Dow Catalyst 9L10, available from Dow Chemical) was first applied to both sides of the film sleeve laid flat, and the film sleeve provided with the adhesive was then laminated on both sides with the functional layer.

The film produced is sterilizable with hot steam and is already permanently heat-sealable with welding tools adjusted to a temperature of 125° C.

Example 3 (Comparative Example According to Example 1 of DE 10361851 A1)

First Polymer Layer (A):
  97% by weight of Moplen® HP525J from Lyondell Basell Corp., USA/polypropylene homopolymer
  3% by weight of Tuftec® H1062 from Asahi Kasei, Japan/styrene-ethylene/butylene block copolymer
  The stated formulation was mixed in the melt state in a separate compounding step and granulated for further use.
Second Polymer Layer (B):
  85% by weight of Bormed® TD109CF from Borealis, Austria/propylene terpolymer
  15% by weight of Tuftec® H1062 from Asahi Kasei, Japan/styrene-ethylene/butylene block copolymer
  The stated formulation was mixed in the melt state in a separate compounding step and granulated for further use.
Central Polymer Layer (C):
  75% by weight of Bormed® TD109CF from Borealis, Austria/propylene terpolymer
  20% by weight of Tuftec® H1062 from Asahi Kasei, Japan/styrene-ethylene/butylene block copolymer
  5% by weight of Engage® 8003, Dow Chemical Company, USA/ethylene-octene polyolefin elastomer
  The stated formulation was mixed in the melt state in a separate compounding step and granulated for further use.
  The film was coextruded on a blown-film line with water cooling using process parameters customary for polypropylene.

The film was made with a total thickness of 200 μm, with the first polymer layer (A) and second polymer layer (B) both having a thickness of 15 μm and the central polymer layer (C) having a thickness of 170 μm. The film produced is sterilizable with hot steam and is permanently heat-sealable with welding tools adjusted to a temperature of 125° C.

Example 4 (not According to the Invention, Comparison)

First Polymer Layer (A):
  97% by weight of Moplen® HP525J from Lyondell Basell Corp., USA/polypropylene homopolymer
  3% by weight of Tuftec® H1062 from Asahi Kasei, Japan/styrene-ethylene/butylene block copolymer
  The stated formulation was homogeneously mixed in the melt state in a separate compounding step, extruded, and granulated for further use.
Second Polymer Layer (B):
  75% by weight of Bormed® LE6600-PH from Borealis, Austria/low-density polyethylene (LDPE)
  20% by weight of Bormed® TD109CF from Borealis, Austria/propylene terpolymer
  5% by weight of Engage® 8003 from Dow Chemical Company, USA/ethylene-octene polyolefin elastomer
  The stated formulation was homogeneously mixed in the melt state in a separate compounding step, extruded, and granulated for further use.
Central Polymer Layer (C):
  70% by weight of Bormed® TD109CF from Borealis, Austria/propylene terpolymer
  20% by weight of Tuftec® H1062 from Asahi Kasei, Japan/styrene-ethylene/butylene block copolymer
  10% by weight of Engage® 8003, Dow Chemical Company, USA/ethylene-octene polyolefin elastomer
  The stated formulation was homogeneously mixed in the melt state in a separate compounding step, extruded, and granulated for further use.

The granulated compounds of the polymer layers (A), (B) and (C) were coextruded on a blown-film line with water cooling using process parameters customary for polypropylene, and a multilayer film was obtained in the form of a film sleeve.

The film was made with a total thickness of 200 μm, with the first polymer layer (A) and second polymer layer (B) both having a thickness of 15 μm and the central polymer layer (C) having a thickness of 170 μm.

Testing of the Weld Strength of Films of Examples 1 to 4

1. (a) Preparation of heat-sealed samples using a film sealing unit (IST Med from Kopp) from 2 films lying on top of one another (each 20×15 cm); weld region (film edge)~15 mm.
   Welding parameters: pressure: 2-3 bar, time: 1-2 seconds, gap: 320 μm. (b) followed by punch-out of 15×80 mm wide test strips with heat-sealed edge (=unsterilized samples).
2. Hot-steam sterilization at 121° C. (WEBECO type A 35 autoclave, 2 bar, 20 minutes) of some of the test strips with heat-sealed edge that have been obtained (=hot steam-sterilized samples). Film cohesion is prevented by opening the non-heat-sealed regions of the test strips beforehand and placing paper in between.
3. Determination of weld strength by clamping the cooled test strips with heat-sealed edge in a tensile testing machine (Zwick iLine 500N from Zwick) and pulling the test strips at a rate of 400 mm/min.
The results for weld assessment are reported in N/15 mm.
The weld strength of the multilayer film should be greater than 25 N/15 mm, preferably greater than 30 N/15 mm. If the weld strength of the multilayer film is 10 to 20 N/15 mm, it has a peelable seam.

FIG. 1 shows weld curves of unsterilized samples according to Examples 1 to 4. The x-axis indicates the welding temperature [° C.]; the y-axis indicates the tensile strength [N/15 mm].

Figure 2:
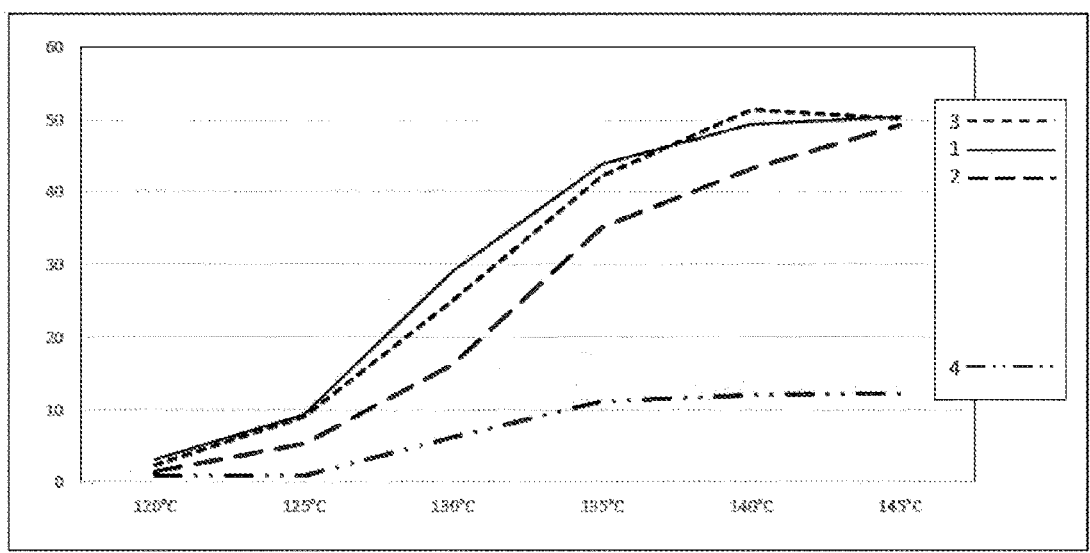
FIG. 2 shows weld curves of hot steam-sterilized samples according to the invention and comparative hot steam-sterilized samples.

FIG. 2 shows weld curves of hot steam-sterilized samples according to Examples 1 to 4. The x-axis indicates the welding temperature [° C.]; the y-axis indicates the tensile strength [N/15 mm].

In the figures, the individual examples are shown by different line structures.

Results (a) Unsterilized Samples
The weld curves (see FIG. 1) of the films of Examples 1, 3 and 4 have a weld strength of >30 N/15 mm at approx. 130° C.; the film of Example 2 having the PET/SiOx functional layer starts to heat-seal (weld strength>30 N/15 mm) at a temperature higher by about 5° C., which is not a problem because of the higher temperature resistance of the film due to the PET/SiOx functional layer.
(b) Hot Steam-Sterilized Samples
The weld curves (see FIG. 2) of the films of Examples 1, 2 and 3 are similar to those of the unsterilized samples, i.e. they have a weld strength of >30 N/15 mm at approx. 130° C. or 135° C.; the film of Example 4 (second polymer layer based on LDPE) does not show the desired weld strength after hot-steam sterilization. It is apparent that the weld is separated or "peeled", or delaminated. If films according to Example 4 were to be used as medical bags, the bags would open during sterilization in an autoclave or when removed.

PE materials such as LDPE or HDPE are incompatible with polypropylene, i.e. in the case of multilayer films having PP-based central layers, the inner layer separates easily from the central layer. Furthermore, the melting temperature of LDPE raw materials is between 110° C. and 115° C., i.e. the raw material melts during hot-steam sterilization and weakens the weld.

Owing to the specific combination used for the second polymer layer (inner layer) B), said combination being that of a polyethylene-based composite B1), a PP terpolymer B2) and a polyethylene elastomer B3) (as adhesion promoter), the multilayer film according to the invention in accordance with Examples 1 and 2 is shown to have the advantage that the inner layer B) cannot be easily detached from the central layer C); furthermore, the composite B1) used is shown not to melt during hot-steam sterilization, the weld strength consequently remaining sufficiently high.

Compared to the prior-art multilayer films in accordance with Example 3 (inner layer B composed of impact-modified propylene terpolymer), the multilayer films of Examples 1 and 2 according to the invention have a very good impact strength even without the addition of an impact modifier—owing to the polyethylene-based composite B1) used for the inner layer B)—and they have a comparable weld strength and suitability for hot-steam sterilization. Furthermore, multilayer films according to the invention have the advantage over those in accordance with Example 3 that active ingredients are less strongly adherent to the PE-containing inner layer, i.e. the so-called "recovery value" is higher.

The invention claimed is:
1. A heat-sterilizable multilayer film comprising
   a) a first polymer layer (A) containing at least one propylene homopolymer modified with at least one impact modifier;

b) a second polymer layer (B) containing:

B1) 60% to 85% by weight, based on (B), of a homogeneous composition (B1) consisting of:

B11) 65% to 85% by weight, based on (B1), of ethylene homopolymer, and

B12) 15% to 35% by weight, based on (B1), of at least one ethylene copolymer which contains as comonomer at least one alpha-olefin having 4 to 12 carbon atoms, where (B1) has a melting temperature (determined by Differential Scanning calorimetry (DSC)) of >125° C. and a density (in accordance with DIN EN ISO 1183-1 (2019-09)—Method B) of 945 to 960 kg/m$^3$;

B2) 11% to 30% by weight, based on (B), of at least one propylene terpolymer; and B3) 4% to 15% by weight, based on (B), of at least one polyethylene elastomer which is a copolymer of ethylene with at least one alpha-olefin having 4 to 12 carbon atoms; and c) a central polymer layer (C) situated between the first polymer layer (A) and the second polymer layer (B), containing:

C1) 61% to 80% by weight, based on (C), of at least one propylene terpolymer;

C2) 15% to 25% by weight, based on (C), of at least one styrene block copolymer elastomer; and C3) 5% to 19% by weight, based on (C), of at least one polyethylene elastomer which is a copolymer of ethylene with at least one alpha-olefin containing 4 to 12 carbon atoms.

2. The heat-sterilizable multilayer film of claim 1, wherein the homogeneous composition (B1) consists of:

B11) 70% to 80% by weight, and

B12) 20% to 30% by weight.

3. The heat-sterilizable multilayer film of claim 1, wherein the ethylene copolymer (B12) is prepared by copolymerization of ethylene and at least one alpha-olefin in the presence of a metallocene catalyst.

4. The heat-sterilizable multilayer film of claim 1, wherein the ethylene homopolymer (B11) used is a high-density polyethylene (HDPE).

5. The heat-sterilizable multilayer film of claim 1, wherein the ethylene copolymer (B12) contains 25% to 40% by weight of at least one alpha-olefin comonomer.

6. The heat-sterilizable multilayer film of claim 1, wherein the ethylene copolymer (B12) contains as comonomer at least one alpha-olefin selected from 1-butene, 1-pentene, 1-hexene, and 4-methyl-1-pentene.

7. The heat-sterilizable multilayer film of claim 1, wherein the component (B2) and/or (C1) is a terpolymer of propylene, ethylene, and/or C4 to $C_{16}$ α-olefins.

8. The heat-sterilizable multilayer film of claim 1, wherein the component (B3) is a copolymer of ethylene with an alpha-olefin having 7 to 12 carbon atoms.

9. The heat-sterilizable multilayer film of claim 1, wherein the second polymer layer (B) contains:

B1) 65% to 80% by weight;

B2) 15% to 25% by weight; and

B3) 4% to 12% by weight.

10. The heat-sterilizable multilayer film of claim 1, wherein the central polymer layer (C) contains:

C1) 65% to 75% by weight;

C2) 17% to 22% by weight; and

C3) 8% to 17% by weight.

11. The heat-sterilizable multilayer film of claim 1, wherein the styrene block copolymer (SBC) elastomer (C2) is selected from the group consisting of: styrene-ethylenebutylene-styrene block copolymer (SEBS), styrene-ethylene-propylene-styrene block copolymer (SEPS), styrene-ethylene-ethylene-propylene-styrene block copolymer (SEEPS), styrene-isoprene-styrene block copolymer (SIS), and styrene-butadiene-styrene block copolymer (SBS).

12. The heat-sterilizable multilayer film of claim 1, wherein the polyethylene elastomer (C3) is an ethylene-butylene copolymer and/or an ethylene-octene copolymer.

13. The heat-sterilizable multilayer film of claim 1, wherein the multilayer film consists of the polymer layers (A), (B), and (C), and the total film thickness of the multilayer film ranges from 50 to 500 μm, and, based in each case on the total film thickness of the multilayer film, the layer thickness of the first polymer layer (A) is 5% to 15% by weight;

the layer thickness of the second polymer layer (B) is 5% to 15% by weight; and the layer thickness of the central polymer layer (C) is 70% to 90% by weight.

14. A method for producing the heat-sterilizable multilayer film of claim 1, wherein the first polymer layer (A), the central polymer layer (C), and the second polymer layer (B) are coextruded.

15. The heat-sterilizable multilayer film of claim 1, comprising an additional functional layer (D) adjacent to the first polymer layer (A) on the outer side of (A) and wherein the functional layer (D) contains at least one material selected from the group consisting of: ethylene-vinyl alcohol copolymers, polyvinyl alcohols, polyamides, liquid crystal polymers (LCP), aromatic polyesters, silicon oxide ($SiO_x$), aluminum oxide ($AlO_x$), and acrylate-based polymers.

16. The heat-sterilizable multilayer film of claim 15, wherein the functional layer (D) consists of $PET/SiO_x$.

17. A method for producing a laminated multilayer film sleeve made of the heat-sterilizable multilayer film of claim 15, comprising the following steps:

(a') producing a film sleeve made of a multilayer film, wherein the first polymer layer (A), the central polymer layer (C), and the second polymer layer (B) are coextruded, and wherein the interior of the film sleeve is flooded with air;

(b') optionally cooling the film sleeve produced in method step (a');

(c') coating the optionally cooled film sleeve with a pressure-sensitive adhesive layer on at least one side of the first polymer layer (A) of the film sleeve;

(d') optionally drying the film sleeve provided with the pressure-sensitive adhesive layer;

(e') laminating the at least one side of the first polymer layer (A) of the film sleeve coated with the pressure-sensitive adhesive layer with the functional layer (D); and (f) optionally drying and curing the laminated film sleeve.

18. A medical package comprising the heat-sterilizable multilayer film of claim 1.

19. A method for producing the medical package made of the heat-sterilizable multilayer film of claim 1, comprising the steps of:

a) providing at least one heat-sterilizable multilayer film, wherein the first polymer layer (A), the central polymer layer (C), and the second polymer layer (B) are coextruded;

b) optionally providing one or more port elements and/or flexible tubes;

c) shaping the medical package from the at least one heat-sterilizable multilayer film, wherein the second polymer layer (B) forms the inner face of the medical package and the first polymer layer (A) forms the outer face of the medical package;

d) optionally positioning the port elements and/or flexible tubes between the inner faces at the contours of the medical package;

e) contacting the inner faces with one another and with port elements and/or flexible tubes optionally positioned in between at the contours of the medical package; and f) heat-sealing the inner faces with one another and with port elements and/or flexible tubes optionally positioned in between at the contours of the medical package.

20. A method for producing the medical package made of the heat-sterilizable multilayer film of claim 1, comprising the steps of:

a) providing at least one heat-sterilizable multilayer film;

b) optionally providing one or more port elements and/or flexible tubes;

c) shaping the medical package from the at least one heat-sterilizable one multilayer film, wherein the second polymer layer (B) forms the inner face of the medical package and the first polymer layer (A) forms the outer face of the medical package;

d) optionally positioning the port elements and/or flexible tubes between the inner faces at the contours of the medical package;

e) contacting the inner faces with one another and with port elements and/or flexible tubes optionally positioned in between at the contours of the medical package; and f) heat-sealing the inner faces with one another and with port elements and/or flexible tubes optionally positioned in between at the contours of the medical package, wherein the heat-sterilizable multilayer film is produced by the following steps:

(1) producing a film sleeve made of a multilayer film, wherein the first polymer layer (A), the central polymer layer (C), and the second polymer layer (B) are coextruded, and wherein the interior of the film sleeve is flooded with air;

(2) optionally cooling the film sleeve produced in method step (1);

(3) coating the optionally cooled film sleeve with a pressure-sensitive adhesive layer on at least one side of the first polymer layer (A) of the film sleeve;

(4) optionally drying the film sleeve provided with the pressure-sensitive adhesive layer;

(5) laminating the at least one side of the first polymer layer (A) of the film sleeve coated with the pressure-sensitive adhesive layer with the functional layer (D); and (6) optionally drying and curing the laminated film sleeve.

21. A medical package comprising the heat-sterilizable multilayer film of claim 15.

22. A method for producing the medical package made of the heat-sterilizable multilayer film of claim 15, comprising the steps of:

a) providing at least one heat-sterilizable multilayer film, wherein the first polymer layer (A), the central polymer layer (C), and the second polymer layer (B) are coextruded;

b) optionally providing one or more port elements and/or flexible tubes;

c) shaping the medical package from the at least one heat-sterilizable multilayer film, wherein the second polymer layer (B) forms the inner face of the medical package and the first polymer layer (A) forms the outer face of the medical package;

d) optionally positioning the port elements and/or flexible tubes between the inner faces at the contours of the medical package;

e) contacting the inner faces with one another and with port elements and/or flexible tubes optionally positioned in between at the contours of the medical package; and f) heat-sealing the inner faces with one another and with port elements and/or flexible tubes optionally positioned in between at the contours of the medical package.

23. A method for producing the medical package made of the heat-sterilizable multilayer film of claim 15, comprising the steps of:

a) providing at least one heat-sterilizable multilayer film;

b) optionally providing one or more port elements and/or flexible tubes;

c) shaping the medical package from the at least one heat-sterilizable one multilayer film, wherein the second polymer layer (B) forms the inner face of the medical package and the first polymer layer (A) forms the outer face of the medical package;

d) optionally positioning the port elements and/or flexible tubes between the inner faces at the contours of the medical package;

e) contacting the inner faces with one another and with port elements and/or flexible tubes optionally positioned in between at the contours of the medical package; and f) heat-sealing the inner faces with one another and with port elements and/or flexible tubes optionally positioned in between at the contours of the medical package, wherein the heat-sterilizable multilayer film is produced by the following steps:

(1) producing a film sleeve made of a multilayer film, wherein the first polymer layer (A), the central polymer layer (C), and the second polymer layer (B) are coextruded, and wherein the interior of the film sleeve is flooded with air;

(2) optionally cooling the film sleeve produced in method step (1);

(3) coating the optionally cooled film sleeve with a pressure-sensitive adhesive layer on at least one side of the first polymer layer (A) of the film sleeve;

(4) optionally drying the film sleeve provided with the pressure-sensitive adhesive layer;

(5) laminating the at least one side of the first polymer layer (A) of the film sleeve coated with the pressure-sensitive adhesive layer with the functional layer (D); and (6) optionally drying and curing the laminated film sleeve.

* * * * *